(12) United States Patent
Inoue

(10) Patent No.: US 6,760,618 B1
(45) Date of Patent: Jul. 6, 2004

(54) IONTOPHORESIS SYSTEM

(75) Inventor: Kazutaka Inoue, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/664,349

(22) Filed: Sep. 18, 2000

(30) Foreign Application Priority Data

Sep. 20, 1999 (JP) .......................................... 11-265251

(51) Int. Cl.$^7$ ............................. A61N 1/30; H02J 7/00
(52) U.S. Cl. ...................... 604/20; 320/137; 324/427; 607/75
(58) Field of Search ........................... 604/20; 607/75; 324/427; 320/137

(56) References Cited

U.S. PATENT DOCUMENTS 5,688,232 A * 11/1997 Flower .................... 604/20
5,764,034 A * 6/1998 Bowman ................... 320/155
5,834,921 A * 11/1998 Mercke et al. ............ 320/112
6,154,012 A * 11/2000 Drori ....................... 320/162
6,208,891 B1 * 3/2001 Flower

* cited by examiner

Primary Examiner—William Wayner
(74) Attorney, Agent, or Firm—Townsend & Banta

(57) ABSTRACT

An iontophoresis system comprises a power supply apparatus having a chargeable battery, a positive output terminal, a negative output terminal and a positive charge terminal, and a preparation having input terminals connected to output terminals of the power supply apparatus. The negative output terminal of the power supply apparatus also serves as a negative charge terminal for charging the battery. During charging, the preparation is removed, and terminals of a charger are connected to terminals of the power supply apparatus, respectively. The power supply apparatus comprises a power supply monitoring portion which gives a warning when a battery voltage becomes a predetermined value or lower and a control portion for controlling a power supply state from the output terminal.

4 Claims, 4 Drawing Sheets

US 6,760,618 B1

IONTOPHORESIS SYSTEM

BACKGROUND OF THE INVENTION

The present invention relates to an iontophoresis system applied percutaneously or trans-mucosally, and in particular to a portable iontophoresis system.

Iontophoresis is a percutaneous absorption-promoting system which employs electricity for external stimulation. Its principle is such that skin barrier permeability of drug molecules is promoted by movements of positively-charged molecules from an anode to a cathode and those of negatively-charged molecules from the cathode to the anode in an electric field mainly produced between the anode and the cathode by power supply [refer to Journal of Controlled Release, Vol. 18, pages 213 to 220, 1992; Advanced Drug Delivery Review, Vol. 9, page 119, 1992; and Pharmaceutical Research, Vol. 3, pages 318 to 326, 1986].

Thus, in iontophoresis, an anode and a cathode are provided in pair and a current is generated between the anode and cathode, thereby moving a drug. In recent years, a constant current unit is employed so that a current can be maintained at a predetermined value irrespective of an impedance difference due to individual difference. This constant current unit can keep a drug delivery rate constant irrespectively of impedance because the drug delivery rate correlates with a current quantity. A unit of such type is disclosed in Japanese Patent Laid-Open Publication No. 5-245214, for example. In addition, a unit for controlling a drug supply rate with a program as required is disclosed in Japanese Patent Laid-Open Publication No. 7-124265, for example.

In the meantime, in order to achieve a small iontophoresis system suitable to be portable, in particular, it is required to minimize the number of circuit parts of a power supply apparatus and miniaturize the unit. Among them, in particular, it is desired to reduce a battery incorporated in the power supply apparatus in size and in weight. When a small battery is employed, in general, frequent battery replacement is required because of its small battery capacity, which requires a user to do cumbersome operation of battery replacement, and thus, is not preferable. In addition, it is desirable that battery replacement can be avoided as far as possible from an economical aspect or an environmental aspect including disposal of used battery.

Further, another problem with a portable power supply apparatus includes circuit malfunction caused by faults of components. At the time of designing a circuit for the power supply apparatus, safety is taken into account to avoid such discrepancies that, a high output current exceeding a set level is generated or an output cannot be stopped completely when it must be stopped, even if the above malfunction occurs. For example, such a system is disclosed in National Publication of International Patent Application No. 8-505541.

However, when any of the parts constituting a power supply apparatus fails, influence on operation of the power supply apparatus greatly differs depending on which of these parts fails. When a power supply apparatus itself cannot identify a failure, a user may use the failed unit repeatedly until the failure is found. In order to overcome these problems, a large-scale circuit is generally required, which acts against reductions in size and weights of a power supply apparatus.

SUMMARY OF THE INVENTION

In view of the foregoing circumstance, an object of the present invention is to provide a small and light iontophoresis system with superior usability.

The present inventors made efforts earnestly to reduce an iontophoresis system in size and weight. As a result, they found out that if a small secondary battery is employed for a power supply and at least one of charge terminals for charging the battery is also used as an output terminal, a small and light-weight iontophoresis system with superior usability could be used, and accomplished the present invention.

An iontophoresis system according to the present invention comprises a power supply apparatus having a chargeable battery and a plurality of output terminals and a preparation which is connected to the output terminals of the power supply apparatus and which is adopted to administer a drug percutaneously or trans-mucosally, wherein at least one of the output terminals of the power supply apparatus is also used as a charge terminal for charging the battery. Here, a secondary lithium battery, for example, is employed as a chargeable battery.

An iontophoresis power supply apparatus according to the present invention comprises a chargeable battery, a plurality of output terminals for outputting electric energy from the battery, and a charge terminal for charging the battery, wherein at least one of the output terminals is also used as a charge terminal. In addition, the present iontophoresis power supply apparatus preferably comprises a power supply monitoring portion that monitors a battery voltage and gives warning when the battery voltage becomes a predetermined value or lower. Further, the present power supply apparatus preferably comprises a control portion for controlling power supply of electric energy outputted from the output terminals. The control portion is adopted to record a power supply state of electric energy or to externally incorporate a program for power supply control of electric energy.

An iontophoresis charger according to the present invention is adopted to charge a battery of the iontophoresis power supply apparatus. This charger comprises an operational check portion which performs operational check of the power supply apparatus based on an inputted power supply record of the electric energy outputted from the power supply apparatus. This charger can comprise a display portion for displaying a power supply record of the power supply apparatus. In addition, the charger may comprise a program storage portion that stores a program for power supply control of the power supply apparatus.

DETAILED DESCRIPTION OF THE PREFERRED EMBODIMENTS

Hereinafter, embodiments of an iontophoresis system according to the present invention will be described in detail with reference to the accompanying drawings.

Figure 1:
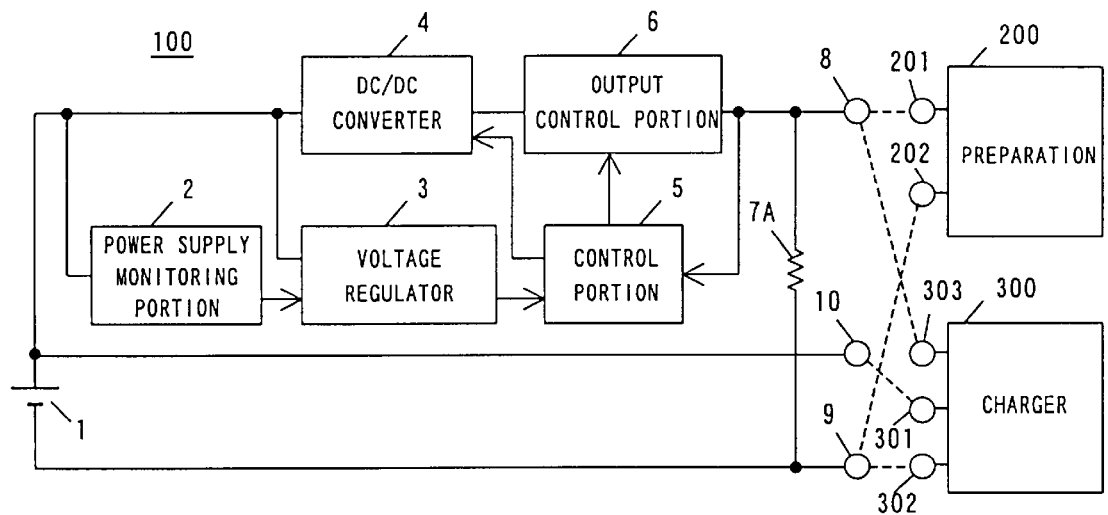
FIG. 1 is a view showing one embodiment of an iontophoresis system according to the present invention.

FIG. 1 is a view showing one embodiment of an iontophoresis system according to the present invention. In this system, an iontophoresis power supply apparatus 100 is connected to a preparation 200 during driving. During power charging, the preparation 200 is removed and a charger 300 is connected to the power supply apparatus 100 instead.

The power supply apparatus 100 in the illustrative embodiment comprises three terminals, i.e., a positive (anode side) output terminal 8, a negative (cathode side) output terminal 9 also serving as a charger, and a positive charge terminal 10. Here, the negative output terminal 9 also serving as a charger, functions as a negative output terminal during system driving, and functions as a negative charge terminal during charging. As illustrated, the positive output terminal 8 is connected to the anode side of a battery 1 via an output control portion 6 and a DC/DC converter 4, and the negative output terminal 9 is connected to cathode side of the battery 1. In addition, the positive charge terminal 10 is connected to the anode side of the battery 1. The DC/DC converter 4 and output control portion 6 are controlled by a signal from a control portion 5. The control portion 5 inputs signals from the power monitoring portion 2 and voltage regulator 3 as well as an output of the output control portion 6.

Here, a coin-shaped secondary lithium battery, for example, is employed as the battery 1 without being limited thereto. The power supply monitoring portion 2 is composed of a voltage monitoring IC, for example. When a battery voltage is a predetermined value or lower, a signal for warning a lowered battery voltage is outputted to the control portion 5. The voltage regulator 3 is composed of a three-terminal regulator for smoothing a battery voltage, for example, and for supplying a predetermined voltage to the control portion 5. The DC/DC converter 4 comprises a switching regulator for increasing the voltage of the battery 1 to a predetermined output voltage by generation and/or accumulation of back electromotive force of a coil, for example. The control portion 5 is composed of a microcomputer, a memory or the like, and controls start/stop of this apparatus, output supply/interruption, and an output voltage/output current or the like. The output control portion 6 is an output control switch for supplying or interrupting an output from the DC/DC converter 4 to the output terminal in accordance with a control signal from the control portion 5, and is composed of a transistor or the like.

The power supply state of electric energy outputted from the output control portion 6 is recorded in an internal memory by means of the control portion 5. In addition, the control portion 5 can add communication features so that a power supply record can be transmitted to the charger 300 and a program for setting a power supply pattern can be received from the charger 300.

A resistor 7A is a pull-down resistor for fixing the positive output terminal 8 to a voltage that the control portion 5 recognizes as a voltage of a predetermined value or lower (hereinafter, referred to as "L" level) when an output of the power supply apparatus 100 is stopped, and is connected between the positive output terminal 8 and the negative output terminal 9. When the charger 300 is connected to the power supply apparatus 100, the positive output terminal 8 is set to a voltage that the control portion 5 recognizes as a voltage of a predetermined value or higher (hereinafter, referred to as an "H" level). Component parts such as hooks or magnets, which are used both for power conduction and fixing, are preferably employed for the positive output terminal 8 and the negative output terminal 9. Component parts for the positive charge terminal 10 may have a structure with an exposed metal face.

The preparation 200 comprises a drug containing electrode portion connected to a positive input terminal 201 and an opposite electrode portion connected to a negative input terminal 202. The preparation 200 of this type is described in Japanese Patent Laid-Open Publication No. 2-241464, for example. In addition, the charger 300 comprises positive and negative charge terminals 301 and 302 and a control terminal 303.

Figure 2:
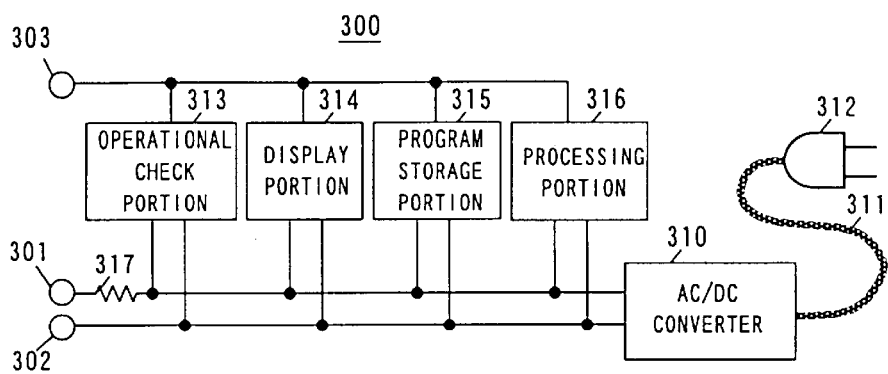
FIG. 2 is a block diagram depicting an example of configuring a charger according to the present invention.

FIG. 2 is a block diagram depicting an example of configuration of a charger 300 according to the present invention. As shown in the figure, the charger 300 comprises an AC/DC converter 310 in which a direct current output side is connected to the positive and negative charge terminals 301 and 302, a power cable 311 and a plug 312 which are connected to an alternating current input side of the AC/DC converter 310, an operational check portion 313 connected to the control terminal 303, a display portion 314; a program storage portion 315; a processing portion 316 for performing processing of each of these portions, and a fixed resistance 317 connected to the side of the operational check portion 313 of the positive charge terminal 301. The plug 312 can be connected to a 100V receptacle for home use, and the AC/DC converter 310 outputs a 3V direct current voltage, for example. The operational check portion 313 inputs a power supply record of the electric energy outputted from the power supply apparatus 100 via the control terminal 303, and performs operational check of whether or not the power supply apparatus 100 operates normally based on this power supply record. The display portion 314 is composed of a liquid crystal display, for example, capable of displaying this power supply record. The program storage portion 315 stores a program for power supply control of the electric energy employed in the power supply apparatus 100, and transmits a desired program via the control terminal 303 upon a request from the power supply apparatus 100. These are executed by the processing portion 316.

Now, a description will be given to means for charging in an interface between the power supply apparatus 100 and the charger 300 and for operational check of a circuit, by citing an example. During charging, the input terminals 201 and 202 of the preparation 200 are removed from the positive output terminal 8 and the negative output terminal 9 of the power supply apparatus 100. Then, the charge terminals 301 and 302 and a control terminal 303 are connected respectively to the positive terminal 10, the negative output terminal 9, and the positive output terminal 8 of the power supply apparatus 100. Power is charged to the battery 1 via the charge terminals 301 and 302 of the charger 300.

If a voltage level at the positive output terminal 8 is at an "L" level prior to charging, the voltage is increased to an "H" level by charging with the charger 300. The control portion 5 that has detected the "H" level outputs a control signal to the DC/DC converter 4 and the output control portion 6, and activates the apparatus. The control portion 5 controls the voltage, current, ON/OFF switching or the like at each set value in accordance with a predetermined pattern or protocol. The charger 300 inputs an output from the power supply apparatus 100 or its record via the positive output terminal 8 and the control terminal 303, and checks whether or not an output or power supply is correct at the operational check portion 313. The operational check portion 313 displays a blue light when an output or power supply is correct or displays a red light if it is not correct by employing a light emitting diode (LED) or the like. In addition, this output or power supply record can be displayed on the display portion 314 composed of a liquid crystal display or the like, for example. When a power supply pattern employed in the power supply apparatus 100 is changed, an operator selects a desired power supply pattern of the program storage portion 315 by key input, for example, whereby a program of a desired power supply pattern is transmitted to the control portion 5 of the power supply apparatus 100 via the control terminal 303.

Figure 3:
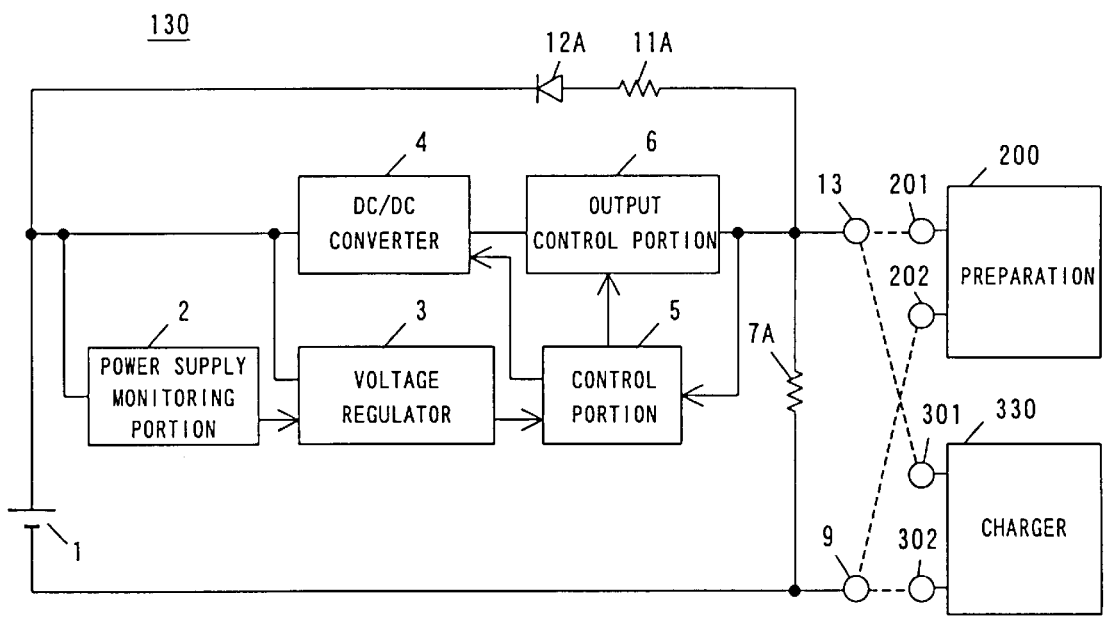
FIG. 3 is a view showing another embodiment of an iontophoresis system according to the present invention.

FIG. 3 is a view showing another embodiment of an iontophoresis system according to the present invention. A power supply apparatus 130 according to this embodiment is composed of two terminals, i.e., a positive output terminal also serving as a charger 13 and a negative output terminal also serving as a charger 9. Here, the positive output terminal also serving as a charger 13 and the negative output terminal also serving as a charger 9 function as output terminals, respectively, during system driving, and function as charge terminals during charging. In this figure, the same reference numerals shown in FIG. 1 denote the same elements. In this embodiment, there are provided a resistor 11A and a diode 12A that are serial connected between the anode side of the battery 1 and the positive output terminal 13. An advantage of this circuit is that only a resistor 11A and a diode 12A may be employed as additional charging parts, and that the positive charge terminal 10 shown in FIG. 1 can be eliminated.

Figure 4:
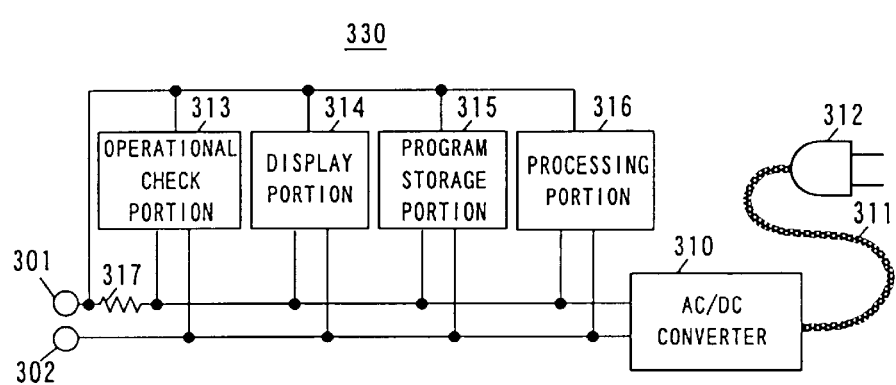
FIG. 4 is a block diagram depicting another example of configuring a charger according to the present invention.

FIG. 4 is a block diagram depicting an example of configuration of a charger 330 according to the present invention, the charger being employed here. In such configuration, an impedance of an output signal of the charger 330 is adjusted, whereby operational check during charging can be made. That is, in FIG. 4, the positive charge terminal 301 is also used as the control terminal 303, and these terminals are connected to each other in the charger 330. In addition, a current supplied to the connection point is regulated by a fixed resistor 317. In such circuit configuration, the operational check portion 313 controls a voltage of the positive charge terminal 301 as an N-ch open drain output, whereby a signal can be transmitted or received even during charging.

Figure 5:
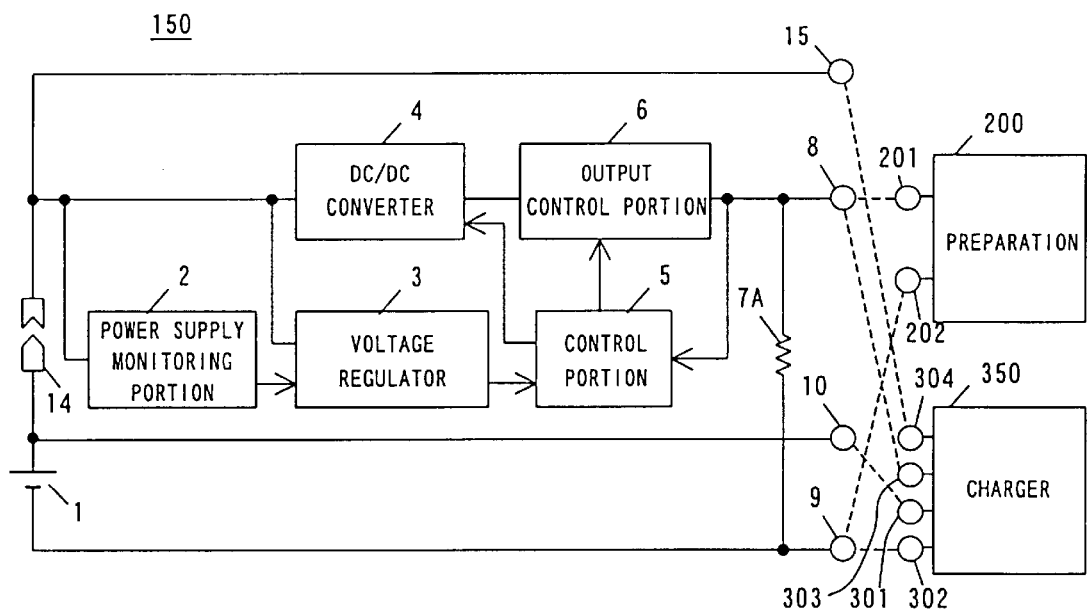
FIG. 5 is a view showing another embodiment of an iontophoresis system according to the present invention.

FIG. 5 is a view showing another embodiment of an iontophoresis system according to the present invention. A power supply apparatus 150 according to the present embodiment comprises four terminals, i.e., a positive output terminal 8, a negative output terminal also serving as a charger 9, a positive charge terminal 10, and a test terminal 15. Here, the negative output terminal also serving as a charger 9 functions as an output terminal during system driving, and functions as a negative charge terminal during charging. In this figure, the same reference numerals shown in FIG. 1 denote the same elements. In this embodiment, an on/off switch 14 and the test terminal 15 are provided. The on/off switch 14 is provided to interrupt power supply from the battery 1 to each portion during charging. The on/off switch 14 may be an electric switch such as FET (field effect transistor) or may be a mechanical contact such that power continuity is interrupted when this apparatus is mounted on the charger.

Figure 6:
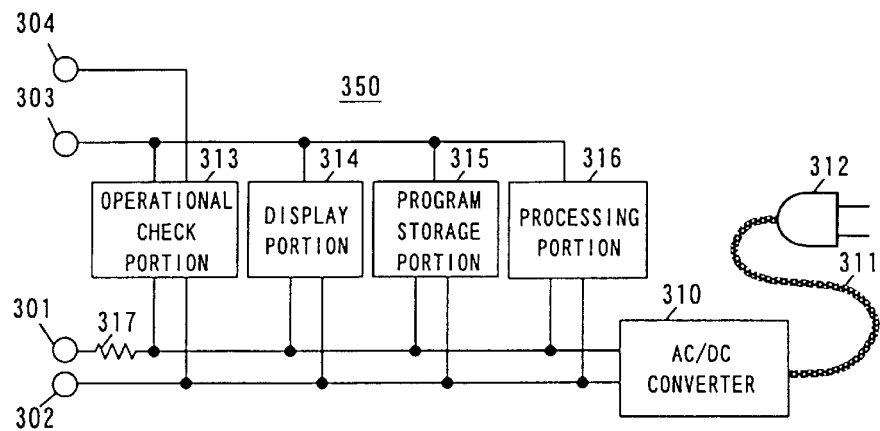
FIG. 6 is a block diagram depicting another example of configuring a charger according to the present invention.

FIG. 6 is a block diagram depicting an example of configuration of a charger 350 according to the present invention, the charger being employed here. During charging, when power supply from the battery 1 to each portion is interrupted by opening the on/off switch 14 of the power supply apparatus 150, the test terminal 15 is interrupted from the battery 1. Thus, the charger 350 can make operational check of the power supply monitoring portion 2 and the voltage regulator 3. This operational check is made by employing the test terminal 15 in which an adjusted output voltage from the charger 350 is set to a power voltage of the power supply apparatus 150. That is, in FIG. 6, an output from the operational check portion 313 is supplied to the power supply apparatus 150 via a power supply terminal 304 and a test terminal 15. Information concerning an output signal of the power supply monitoring portion 2 when the supplied voltage is changed and an output voltage of the voltage regulator 3 is read by the operational check portion 313 via the control portion 5, the output control portion 6, the positive output terminal 8, and the control terminal 303, thereby making operational check.

Figure 7:
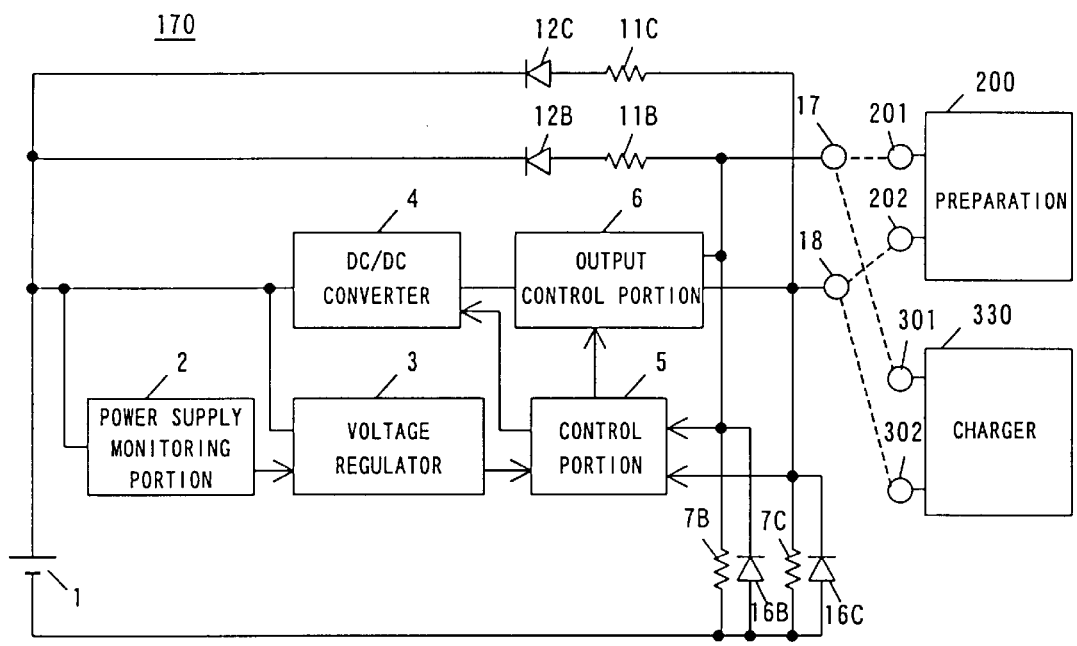
FIG. 7 is a view showing another example of an iontophoresis system according to the present invention.

FIG. 7 is a view showing another embodiment of an iontophoresis system according to the present invention. A power supply apparatus 170 according to this embodiment is composed of two terminals, i.e., a positive and negative output terminal also serving as a charger 17 and a positive and negative output terminal also serving as a charger 18. Here, the positive and negative output terminal also serving as a charger 17 and a positive and negative output terminal also serving as a charger 18 function as output terminals, respectively, during system driving, and functions as charge terminals during charging. In this figure, the same reference numerals shown in FIG. 1 denote the same elements. In this embodiment, there are provided a resistor 11B and a diode 12B which are connected in series between the anode side of the battery 1 and the positive and negative output terminal also serving as a charger 17, a resistor 11C and a diode 12C which are connected in series between the anode side of the battery 1 and the positive and negative output terminal also serving as a charger 18, a resistor 7B and a diode 16B which are connected in parallel between the cathode side of the battery 1 and the positive and negative output terminal also serving as a charger 17, and a resistor 7C and a diode 16C which are connected in parallel between the cathode side of the battery 1 and the positive and negative output terminal also serving as a charger 18, respectively.

In the embodiment shown in FIG. 7, a power supply apparatus 170 is employed as a positive and negative inverting type apparatus. During system driving, the output polarity can be arbitrarily changed by means of the positive and negative output terminals also serving as chargers 17 and 18. In addition, during charging, when a charger 330 is connected to the positive and negative output terminals also serving as chargers 17 and 18, one positive and negative charge terminal enters an "H" level, and the other enters an "L" level by way of an output signal from the charger 330. Here, in the case where the positive and negative output terminal also serving as a charger 17 indicates the "H" level, the signal is inputted to the control circuit 5 in the same way as each portion, and similar operational check is made. In addition, by way of the "H" level signal, a closed circuit is formed by diodes 12B and 16C, and the battery 1 is charged. Further, in the case where the positive and negative output terminal also serving as a charger 18 indicates the "H" level, the closed circuit is formed by resister 11C, diodes 12C and 16B, and the battery 1 is charged.

In this manner, in this embodiment, there is provided a circuit that serves as the positive and negative inverting type apparatus, thereby making it possible to perform charging on both sides. In the case where the power supply apparatus and the charger are mounted in a predetermined direction by mounting means, a closed circuit for charging may be formed in either one direction.

In addition, when battery charging is in progress, a pilot lamp of the power supply apparatus or the charger is lit or blinked, thereby making it possible to display the charging is in progress. Further, an arbitrary function can be added by providing a charger with key input for setting or changing a power supply program.

As described above, in this embodiment, a secondary battery that is a chargeable battery is employed as a battery 1. Secondary batteries include, for example, a nickel-cadmium storage battery, a nickel-hydrogen storage battery, a lithium ion battery, a secondary lithium battery or the like. Here, the respective batteries are characterized as follows.

A nickel-cadmium storage battery is one of the currently most popular secondary batteries. A battery voltage is as low as about 1.2 V. Thus, as a power supply of the control portion composed of microcomputers or the like, it is required to increase pressure or to employ a plurality of batteries. In addition, this type of battery uses cadmium and thus, it has some problem in environmental adoption, though chargeable. However, the battery is characterized by comparatively modest price and high energy capacity. Thus, there is only a little need for paying attention to circuit power reduction, and there is such an advantage that a circuit can be easily configured.

Since a battery voltage of a nickel-hydrogen storage battery is about 1.2 V as low as the nickel-cadmium storage battery, it is required to increase pressure or to employ a plurality of batteries when used as a power supply of the control portion. However, this battery is free of cadmium, thereby making it possible to enhance environmental adoption, difficulty of which is a disadvantage of the nickel-cadmium storage battery. In addition, the battery is superior in that its rectangular shape increases storage efficiency.

A lithium ion battery is comparatively expensive, and the commercially available battery size is larger than the nickel-hydrogen storage battery size. Since its battery voltage is as high as about 3.6 V, a single battery can be employed as a power supply. In addition, this battery is superior in environmental adoption, is characterized by high energy capacity, and has the most excellent performance among from the current batteries.

Various secondary lithium batteries are available. Secondary batteries with about 3 V in battery voltage include a secondary manganese dioxide-lithium battery, a secondary vanadium-lithium battery or the like. Secondary batteries with about 1.5 V in battery voltage include a secondary vanadium-niobium-lithium battery or the like. These batteries are disadvantageous in high internal impedance or small energy capacity, and are small in size and light in weight in comparison with any other secondary battery. Among them, the secondary manganese dioxide-lithium battery and a secondary vanadium niobium lithium battery are preferably employed because the vanadium-lithium secondary battery has quite high internal impedance and low usability. In particular, there are most preferably employed a coin-shaped secondary manganese dioxide-lithium battery with 3 V in battery voltage (ML2016 and ML2032 available from Hitachi Maxel Co., Ltd. and ML1220, ML2016, and ML2430 available from Sanyo Denki Co., Ltd.).

An iontophoresis system according to the present invention is suitable to be portable. Its power supply apparatus is composed of small parts, and performs charging every time the apparatus used in predetermined number. Thus, a coin-shape secondary lithium battery with its low capacity is most preferably employed without being limited thereto.

In addition, in the case where the above secondary lithium battery is employed, a plurality of the batteries may be employed. In the case of a primary battery, it is desired to select a battery size capable of being driven by a single battery because of cumbersome battery replacement and economical aspect. In the case of a secondary battery, when one battery is employed and when two batteries are employed, if its energy capacity and voltage are the same, an optimal battery voltage in the circuit configuration can be selected. In addition, in its storage as well, optimal layout can be provided depending on a structure of the apparatus.

Drugs employed in the preparation 200 of an iontophoresis system according to the present invention are exemplified below.

As an antibiotic, gentamicin sulfate, sisomicin sulfate, tetracycline hydrochloride, ampicillin, cefalotin sodium, cefotiam hydrochloride, cefazolin sodium or the like may be used.

An anti-fungal agent, amorolfine hydrochloride, croconazole hydrochloride or the like may be used. As an anti-lipemic agent, atorvastatin, cerivastatin, pravastatin sodium, simvastatine or the like may be used.

As an agent for the circularatory systems, delapril hydrochloride or the like may be used. As an anti-platelet drug, ticlopidine hydrochloride, cilostazol, aspirin or the like may be used.

As an anti-tumor agent, bleomycin hydrochloride, actinomycin D, mitomycin C, fluorouracil or the like may be used.

As antipyretic, analgesic, and antiphlogistic, ketoprofen, flurbiprofen, felbinac, indometacin sodium, diclofenac sodium, loxoprofen sodium, buprenorphin hydrochloride, eptazocine hydrobromide, pentazocine, butorphanol tartrate, tramadol hydrochloride, morphine hydrochloride, morphine sulfate, fentanyl citrate, fentanyl or the like may be used.

An anti-tussive and expectorant agent, ephedrine hydrochloride, codeine phosphate or the like may be used. As a sedation agent, chlorpromazine hydrochloride, atropine sulfate or the like may be used.

As a muscle relaxant, lanperisone hydrochloride, eperisone hydrochloride, tubocurarine chloride, lanpesorine hydrochloride, eperisone hydrochloride or the like may be used. As an anti-epileptic agent, clonazepam, zonisamide, sodium phenytoin, ethosuximide or the like may be used.

As an anti-ulcer agent, metoclopramide or the like may be used. As an antidepressant, trazodone hydrochloride, imipramine hydrochloride or the like may be used.

As an anti-allergic agent, cetirizine hydrochloride, olopatadine hydrochloride, ketotifen fumarate, azelastine hydrochloride or the like may be used. As an arrhythmic treatment agent, diltiazem hydrochloride, propranolol hydrochloride or the like may be used.

As a vasodilatory agent, tolazoline hydrochloride or the like may be used. As an anti-hypertensive diuretic, metolazone or the like may be used.

As a diabetes treatment agent, pioglitazone hydrochloride, mexiletine hydrochloride, glibenclamide, metoformin hydrochloride or the like may be used.

As an anti-coagulant, sodium citrate or the like may be used. An a styptic, employed menatetrenone, tranexamic acid or the like may be used.

As an anti-tuberculosis agent, isoniazid, ethambutol hydrochloride or the like may be used. As a hormone agent, estradiol, testosterone, prednisolone acetate, dexamethasone sodium phosphate or the like may be used.

As an opioid antagonist agent, levallorphan tartrate, naloxone hydrochloride or the like may be used.

As described above, in an iontophoresis system according to the present invention, the conventional problems such as those concerning battery replacement and disposal caused when a primary battery is employed as a battery of a power supply apparatus are dissolved by employing a secondary battery. In addition, at least one of the charge terminals for charging a battery, which is indispensable, also serves as an output terminal, thereby providing excellent economical aspect, environment adoption, compactness, usability or the like.

In the case of a primary battery, a battery with a high capacity must be employed so that the battery can be repeatedly used to minimize battery replacement and disposal. In the case of a charge type battery, a battery with a low capacity is provided such that one power supply quantity is satisfied, thereby making it possible to ensure miniaturization. Such power supply apparatus of a small size and a light weight is preferably used for a self-adhesive type iontophoresis system in which a power supply apparatus and a preparation are adhered to a living body by adhesiveness of the preparation containing a drug or electrolyte, and is particularly preferable in application over a long period of time. This is because the present invention can reduce discomfort with a user at a projection of the conventional power supply apparatus or peeling a preparation off a living body due to the weight of the power supply apparatus.

Further, a variety of features such as fail safe function is provided in an interface with an accompanying charger, whereby high safety can be provided in spite of a small sized power supply apparatus.

Heretobefore, embodiments of the present invention have been described with reference to the accompanying drawings. The present invention is not limited to these embodiments, and various modifications can occur by one skilled in the art.

According to the present invention, an iontophoresis system with a small size, light weight, and excellent usability can be provided.

What is claimed is:

1. An iontophoresis system comprising:

a power supply apparatus having a chargeable battery and a plurality of output terminals for outputting electric energy from said battery in accordance with a predetermined pattern or protocol; and a preparation which administers a drug percutaneously or transmucosally, being connected to the output terminals of said power supply apparatus, wherein during power charging, said preparation is removed, and at least one of the output terminals of said power supply apparatus also serves as a charge terminal for charging said battery.

2. The iontophoresis system according to claim 1, wherein said battery is a secondary lithium battery.

3. An iontophoresis power supply apparatus comprising a chargeable battery, a plurality of output terminals for outputting electric energy from said battery in accordance with a predetermined pattern or protocol, and a charge terminal for charging said battery, wherein during power charging, said preparation is removed, and at least one of said output terminals also serves as said charge terminal.

4. The iontophoresis power supply apparatus according to claim 3, further comprising a power supply monitoring portion monitoring a voltage of said battery and giving a warning when said battery voltage becomes a predetermined value or lower.

* * * * *